United States Patent
Wolleschensky et al.

(10) Patent No.: US 8,362,448 B2
(45) Date of Patent: Jan. 29, 2013

(54) APPARATUS AND METHOD FOR HIGH SPATIAL RESOLUTION IMAGING OF A STRUCTURE OF A SAMPLE

(75) Inventors: Ralf Wolleschensky, Jena (DE); Helmut Lippert, Jena (DE); Christopher Power, Jena (DE); Benno Radt, Jena (DE)

(73) Assignee: Carl Zeiss Microscopy GmbH, Jena (DE)

(*) Notice: Subject to any disclaimer, the term of this patent is extended or adjusted under 35 U.S.C. 154(b) by 97 days.

(21) Appl. No.: 12/867,291

(22) PCT Filed: Feb. 3, 2009

(86) PCT No.: PCT/EP2009/000677
§ 371 (c)(1),
(2), (4) Date: Oct. 25, 2010

(87) PCT Pub. No.: WO2009/100830
PCT Pub. Date: Aug. 20, 2009

(65) Prior Publication Data
US 2011/0036996 A1    Feb. 17, 2011

(30) Foreign Application Priority Data
Feb. 13, 2008 (DE) .......................... 10 2008 009 216

(51) Int. Cl.
  *G01J 1/58* (2006.01)
(52) U.S. Cl. .................................. 250/459.1; 250/458.1
(58) Field of Classification Search ............... 250/459.1
  See application file for complete search history.

(56) References Cited

U.S. PATENT DOCUMENTS
2004/0095576 A1* 5/2004 Wolleschensky ............. 356/317
(Continued)

FOREIGN PATENT DOCUMENTS
DE    102 57 423      6/2004
DE    10 2006 017 841   10/2007
(Continued)

OTHER PUBLICATIONS

Notification of Transmittal of Translation of International Preliminary Report on Patentability dated Sep. 16, 2010; The International Bureau of WIPO, Switerzland.
Christoph J. Engelbrecht et al., Resolution enhancement in a light-sheet-based microscope (SPIM), Optics Letters, May 15, 2006, vol. 31, No. 10.
(Continued)

*Primary Examiner* — Marcus Taningco
(74) *Attorney, Agent, or Firm* — Frommer Lawrence & Haug LLP

(57) ABSTRACT

Apparatus and method for high spatial resolution imaging of a sample's structure, including a diffraction-limited resolution volume with a plurality of dye molecules which can be switched between different states and have a distribution density which is greater than the inverse of the diffraction-limited resolution volume, where at least one state is fluorescing, the fluorescence being collected by an objective lens and imaged on a spatially resolving detector by an optical system. At least one light source provided for emitting a switching radiation and for emitting an excitation radiation. At least one of the light sources is arranged to radiate through the sample, and a switching and/or fluorescence excitation of the dye molecules is carried out. The switching is a photoactivation or a photodeactivation of the dye molecules. A focusing arrangement is provided for switching and/or for excitation to generate a line-like illumination region extending in a direction of illumination.

37 Claims, 7 Drawing Sheets

U.S. PATENT DOCUMENTS

| | | | |
|---|---|---|---|
| 2006/0012866 A1* | 1/2006 | Wolleschensky | 359/385 |
| 2006/0033987 A1* | 2/2006 | Stelzer et al. | 359/385 |
| 2007/0023686 A1* | 2/2007 | Wolleschensky et al. | 250/458.1 |
| 2007/0109633 A1* | 5/2007 | Stelzer | 359/385 |

FOREIGN PATENT DOCUMENTS

| | | |
|---|---|---|
| EP | 1 617 255 | 1/2006 |
| WO | WO 2004/053558 | 6/2004 |
| WO | WO 2006/127692 | 11/2006 |

OTHER PUBLICATIONS

Jan Huisken et al., "Optical Sectioning Deep Inside Live Embryos by Selective Plane Illumination Microscopy", Science, Aug. 13, 2004, vol. 305, pp. 1007-1009.

Tobia Breuninger et al., "Lateral modulation boosts image quality in single plane illumination fluorescence microscopy", Optics Letters, vol. 32, No. 13, Jul. 1, 2007, pp. 1938-1940.

K. Greger et al., "Basic building units and properties of a fluorescence single plane illumination microscopy", Review of Scientific Instruments, vol. 78, 2007, pp. 023705-1 to 023705-7.

Rainer Heintzmann et al., "Saturated patterned excitation microscopy—a concept for optical resolution improvement", Optical Society of America, vol. 19, No. 8, Aug. 2002, pp. 1599-1609.

Notification Concerning Transmittal of International Preliminary Report on Patentability dated Aug. 26, 2010; The International Bureau of WIPO, Switerzland.

* cited by examiner

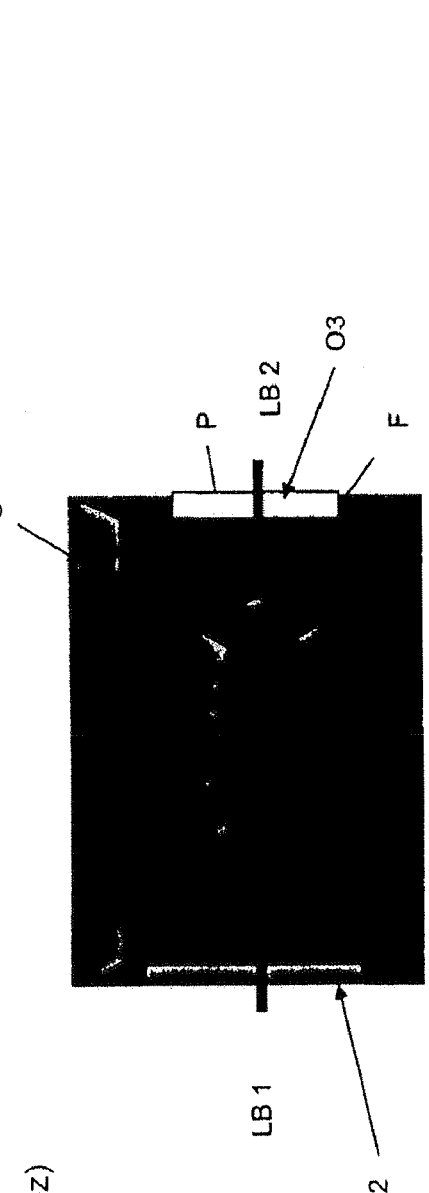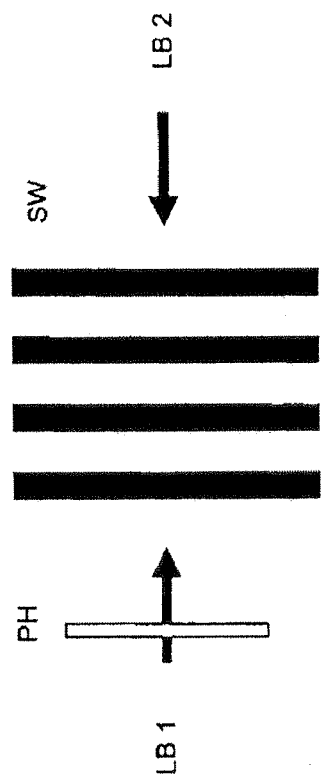
structured activation (and fluorescence excitation)
(plurality of activation beams) for localization of activation in x,z
Fig. 4a - side view (x-z)
Fig. 4b - top view (x-y)

Arrangement for the localization of the activation in z plus deactivation with zero position

APPARATUS AND METHOD FOR HIGH SPATIAL RESOLUTION IMAGING OF A STRUCTURE OF A SAMPLE

The present application claims priority from PCT patent application No. PCT/EP2009/000677 filed on Feb. 3, 2009, which claims priority from German Patent Application No. DE 10 2008 009 216.9 filed on Feb. 13, 2008, the disclosure of which is incorporated herein by reference in its entirety.

BACKGROUND OF THE INVENTION

1. Field of the Invention

The invention is directed to a method and arrangement for realizing a PALM microscope with optimized photoactivation for realizing a higher image rate.

2. Description of Related Art

Selective plane illumination microscopy (SPIM) has been described as a microscopy method, for example, in Stelzer et al. [1-4]:

[1] Stelzer et al., Optics Letters 31, 1477 (2006).
[2] Stelzer et al., Science 305, 1007 (2004).
[3] DE 102 57 423 A1
[4] WO 2004/0530558 A1

Like confocal laser scanning microscopy, SPIM, as a widefield technique, allows three-dimensional objects to be recorded in the form of optical sections, the advantages residing primarily in speed, reduced bleaching out of the sample, and expanded depth of penetration. For this purpose, generally, fluorophores in the sample are excited by laser light which is shaped as a light sheet. The light sheet can be scanned through the sample. A spherical PSF can be generated through the (computational) combination of images recorded from different angles. As a rule, its extent is determined by the lateral resolution of the detection lens that is used, which generally limits the optical resolution that can be achieved in the conventional SPIM method.

Breuninger et al., Optics Letters, Vol. 32, No. 13, 2007, describe the SPIM method with a periodically structured light sheet. The fluorescence excitation is carried out at the locations of high intensity by means of the periodically structured light sheet. The structuring is used for suppressing scattered light from out-of-focus planes and for increasing resolution by structured illumination (see below: Heintzmann et al.).

The method of photoactivated light microscopy (PALM) is described in WO2006/127692. The method is based on the photoactivation of individual molecules which are separated from one another depending on the dimensions of the detection PSFs and highly precise localization thereof by fluorescence detection.

The PALM method, as it is described in WO2006/127692, uses substantially the following main steps to generate a microscope image with a higher optical resolution compared to the standard microscope:

1. Photoactivation of individual molecules: The fluorescence characteristics of the molecules are changed through activation (on/off switching, change in the emission spectrum, . . . ). The activation is carried out in such a way that the distance between activated molecules is greater than or equal to the optical resolution of the standard microscope (given by the Abbe limit).
2. Excitation of the activated molecules and localization of the molecules by a spatially resolving detector.
3. Deactivation of the activated molecules.
4. Repeating steps 1-3 and superimposing the localization points from step 2 which were acquired from different iterative steps to form a high-resolution image.

The activation is preferably carried out in widefield illumination and is statistically distributed. Through the choice of activation energy, it is attempted to achieve (1) as few molecules as possible/no molecules (2) with overlapping Airy disks on the camera (see FIG. 1a). However, overlapping Airy disks are still present and cannot be evaluated ((3) in FIG. 1b). Accordingly, there are regions in which the distance between the activated molecules is larger or very much larger than the Airy disks on the camera (4). Because of the statistical activation of the molecules, approximately 10,000 individual images must be evaluated for generating a high-resolution image to determine the positions of the molecules. Large amounts of data must be processed for this purpose, and measurement is slowed down (approximately 1 minute per high-resolution image). Computation of the individual images to form a high-resolution image requires about 4 hours.

There are difficulties involved in applying the PALM method in three-dimensional imaging because molecules outside of the focus plane are also activated and are therefore bleached and their fluorescent light cannot be used for imaging. Above all, autofluorescent light which is considered an interference signal and causes an extreme reduction in contrast is excited in the entire focus cone in biological samples. This hinders the recording of a z-scan so that three-dimensional imaging of the sample cannot be achieved.

WO2006/127692 describes the use of multiphoton excitation to prevent photoactivation and interfering autofluorescence outside the focus plane. However, the technology is complicated in this arrangement. For example, the dyes (PA-GFP) must be nonlinearly activatable and high intensities must be used which can result in damage to the dye or sample.

Another method that is used to prevent autofluorescence problems is to combine the PALM method with the TIRF technique in which the excitation volume in z-direction is kept very small due to limiting to evanescent waves. However, three-dimensional imaging is not possible with TIRF.

In principle, PALM initially offers only an improved lateral resolution because of the spatially resolved detection. The axial resolution is primarily determined by the extent of the detection PSF that is used. This is another reason for combining PALM with TIRF, which offers a high axial resolution (see also WO2006/127692).

Aside from PALM, other resolution-enhancing methods are known in which the sample is illuminated in such a way that a region detectable through fluorescence is formed which is smaller than corresponds to the Abbe diffraction limit. This is accomplished through a nonlinear interaction based on different methods:

De-excitation of previously excited molecules by stimulated emission (STED, Klar and Hell, Opt. Lett. 24 (1999) 954-956)

De-excitation of previously excited molecules through further excitation into a higher non-fluoresceable state (Excited State Absorption, Watanabe et al., Optics Express 11 (2003) 3271)

Depletion of the ground state by populating with triplets (Ground State Depletion, Hell and Kroug, Appl. Phys. B 60 (1995), 495-497)

Switching a dye between a fluorescing and non-fluorescing state, a less fluorescing state or a fluorescing state characterized in some other way (such as with a different emission wavelength, polarization) (Hell, Jakobs and Kastrup, Appl. Phys. A 77 (2003) 859-860).

In general, these are point-scanning methods having disadvantages with respect to fast data acquisition. Further, the sample is unnecessarily stressed in out-of-focus regions.

As another concept for increasing resolution, Heintzmann et al. (R. Heintzmann, T. M. Jovin and C. Cremer, "Saturated patterned excitation microscopy—a concept for optical resolution improvement", JOSA A 19, 1599-1609 (2002)) suggest a nonlinear process in the form of direct saturation of a fluorescence transition. The increased resolution is based on structured illumination of the sample with periodic grid shapes so that there is a transfer of high object space frequencies into the optical transfer function domain of the microscope. The transfer can be reconstructed indirectly through theoretical post-processing of the data. It is also considered disadvantageous in these methods that the sample is unnecessarily stressed in out-of-focus regions because the structured illumination is performed throughout the entire sample space. Further, the method cannot currently be used with thick samples because the fluorescence excited outside of the focus reaches the detector as a background signal and accordingly reduces the dynamic range.

SUMMARY OF THE INVENTION

The object of the invention is to avoid the disadvantages of the methods described above. The invention describes a method and arrangement for realizing a PALM microscope with optimized photoactivation for realizing a higher image rate. Compared to PALM, a high resolution with three-dimensional imaging is achieved without nonlinear photoactivation. A PALM/TIRF combination for reducing the out-of-focus autofluorescence is not required. The multi-view method (a plurality of illumination angles on the sample) can advantageously be used to achieve an increased depth of penetration and an isotropic optical resolution in x, y, and z.

BRIEF DESCRIPTION OF THE DRAWINGS

FIG. 4a schematically shows another embodiment according to the invention with illumination by means of two light sheets;

FIG. 4b schematically shows a standing wave field as a stripe pattern;

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1B:
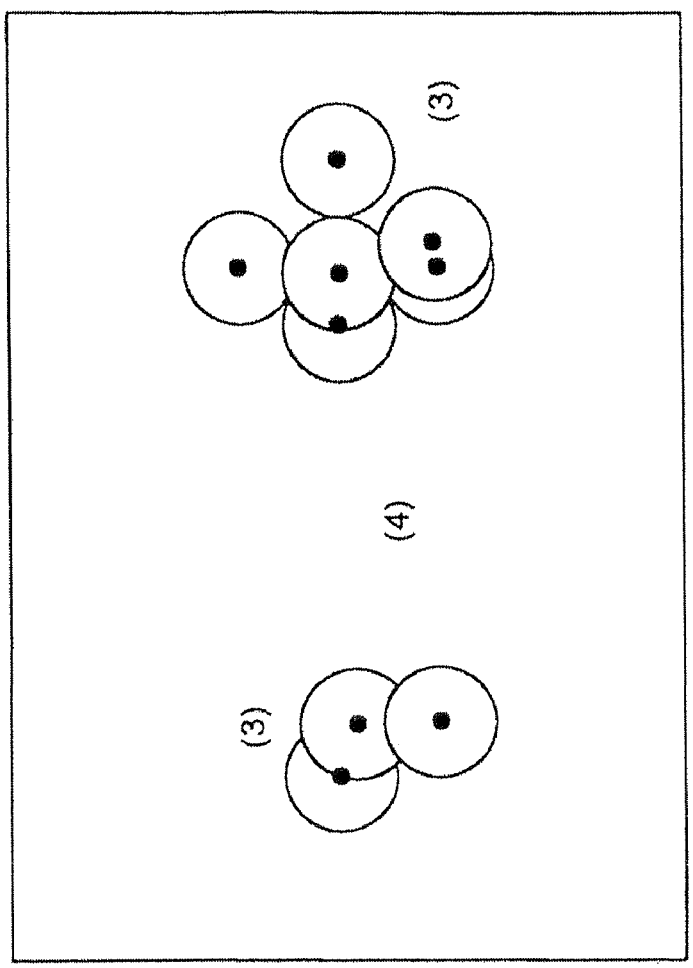
FIG. 1b shows activation of molecules of a sample where there are molecules with overlapping Airy disks with regions in which the distance between the activated molecules is larger or very much larger than the Airy disks.
Figure 1A:
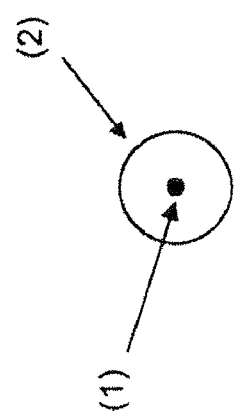
FIG. 1a shows a molecule with an Airy disk.
Figure 2:
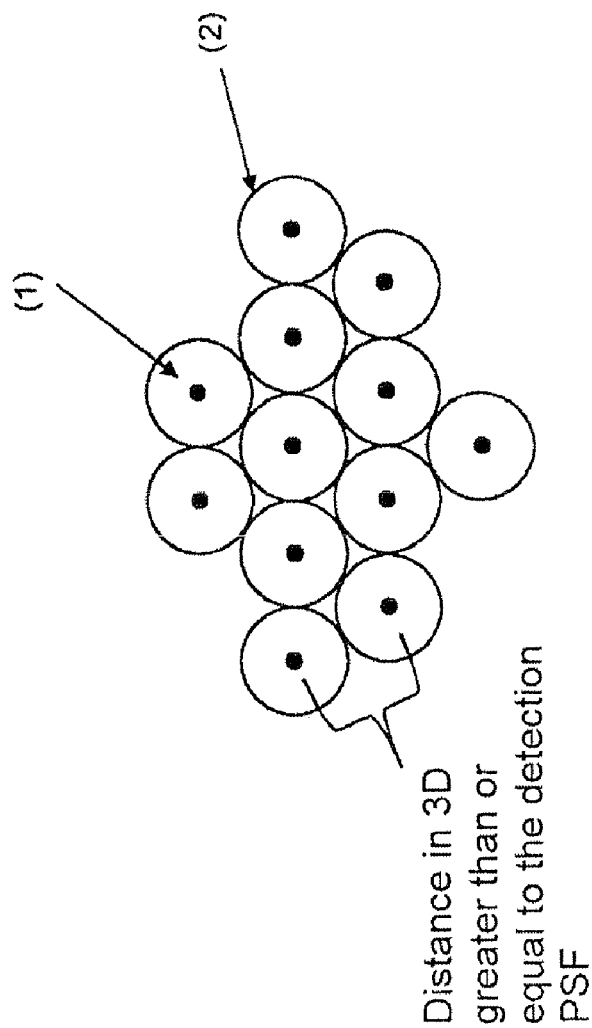
FIG. 2 shows activation of molecules of a sample where there are no molecules with overlapping Airy disks.

As many molecules as possible are activated, according to FIG. 2, without "gaps" ((4) in FIG. 1b) and without the Airy disks of the molecules overlapping on the camera ((3) in FIG. 1b). If the Airy disks of the individual molecules are set end to end, there is preferably a dense packing of spheres. In this way, the speed of the PALM method is increased and the quantity of individual images is reduced.

The arrangements according to the invention and their effects and advantages are described in more detail with reference to FIGS. 3 to 7.

The invention advantageously proposes a surprisingly advantageous combination of the SPIM method with the PALM method.

Figure 3:
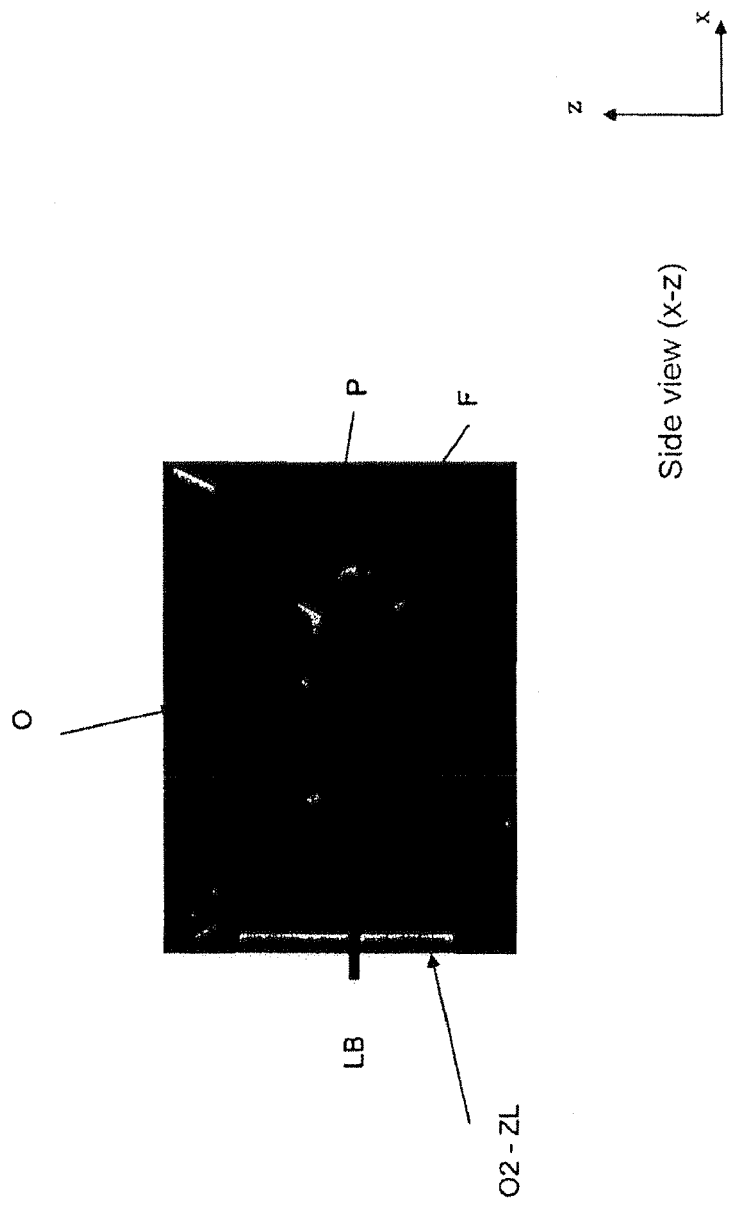
FIG. 3 shows a schematic side view of a flat light sheet.

FIG. 3 is a schematic side view (the radiation direction is the same as the viewing direction) of a flat light sheet LB which is generated, for example, by a cylindrical lens (O2-ZL) and goes through the sample (P).

Above the sample is an objective lens O of a microscope, for example, a widefield microscope with a CCD camera, a laser scanning microscope, or a microscope with structured illumination.

In FIG. 3, a photoactivation is carried out perpendicular to the optical axis of the fluorescence excitation and fluorescence detection by means of the light sheet LB in the form of the SPIM light sheet which is radiated laterally into the sample and lies substantially exactly in the focus plane (F) of the objective lens O. The fluorescence excitation can be carried out only within the focus plane (F). The fluorescence excitation and fluorescence detection are carried out by the microscope objective lens O according to WO2006/127692. Accordingly, there is a localized excitation in the z-direction and samples can be analyzed three-dimensionally without nonlinear photoactivation by the PALM method.

The width of the light beam for photoactivation, i.e., its extent in z-direction, is adapted in such a way that it is advantageously less than or equal to the axial extent of the PSF determined by the numerical aperture of the objective lens O. In this way, activation and bleaching of fluorescence molecules outside the focus plane is avoided in an advantageous manner. In addition, fluorescence can only come from this plane defined by the activation beam. Therefore, this arrangement is inherently three-dimensionally resolving.

The detection is carried out by conventional means such as, for example, by conventional widefield microscopy, confocal microscopy or structured illumination (ZEISS APOTOM).

However, the problem arises in this connection that the excitation beam may excite autofluorescence over the entire sample space. This can be prevented in that, additionally, the light beam for exciting fluorescence (after photoactivation) is radiated in FIG. 3 by a light sheet (LB) perpendicular to detection by means of O2-ZL. This ensures that no out-of-focus autofluorescence signals are generated with an interfering effect on imaging. In addition, the fluorescent light can be detected in a particularly efficient manner separately from the excitation light because there is no need for spectral separation by means of a dichroic beamsplitter. With some switchable dyes such as DENTRA, for example, the photoactivation and fluorescence excitation are carried out with the same wavelength. This can accordingly be realized in a particularly simple manner.

In another conceivable arrangement, the photoactivation is carried out by means of the objective lens O and the fluorescence excitation is carried out by means of the laterally incident light sheet O2. The objective lens O also serves for detection. Again, out-of-focus autofluorescent light is prevented in this case. Out-of-focus autofluorescence which is generated by the activation beam can be spectrally separated, but particularly also temporally separated (the fluorescence excitation is carried out after activation), from the actual fluorescence signal of interest.

A problem in this method is that activated molecules are generated outside of the focus. Therefore, it is advantageous in this method to use molecules which can be deactivated after recording an image plane over the entire sample area, e.g., by means of widefield illumination.

The recording of the high-resolution image for the arrangements according to the invention is carried out as described in WO2006/127692 by the above-mentioned steps 1-4. Fluorescing proteins known from the prior art such as PA-GFP or DRONPA are preferably used as activatable fluorescent dyes. The photoactivation is carried out at 405 nm, the fluorescence excitation is carried out at 488 nm, and the detection is carried out in the range above 490 nm. Further, reversibly switchable synthetic dyes such as Alexa/Cyan constructs can also be used.

Another arrangement according to the invention with illumination by means of two light sheets LB 1 and LB 2 is shown schematically in FIG. 4a. By means of interferometric superposition of light sheets from a plurality of directions (but in the focus plane defined by the detection), an interference pattern is formed along the x-direction in the focus plane. The light sheets can again contain laser light for photoactivation and/or fluorescence excitation. A standing wave field (SW), shown schematically in FIG. 4b as a stripe pattern, is formed as a result of the overlapping. If two light sheets, for example, are used for the photoactivation, the distance between the fluorescence emitters to be actuated can be made greater than or equal to the width of the PSF of the detection (O in FIG. 4a). Preferably, this does not result in any fluorescence emitters which spatially overlap along the x-direction and which, in addition, are localized in z-direction at the location of the focus plane F. Detection is again carried out analogously to the arrangement according to FIG. 3. A displacement of the standing wave field in the focus plane for illuminating the sample in the intensity minima is carried out by adjusting the relative phase between the two light sheets, for example, with a phase modulator (PH).

Figure 5:
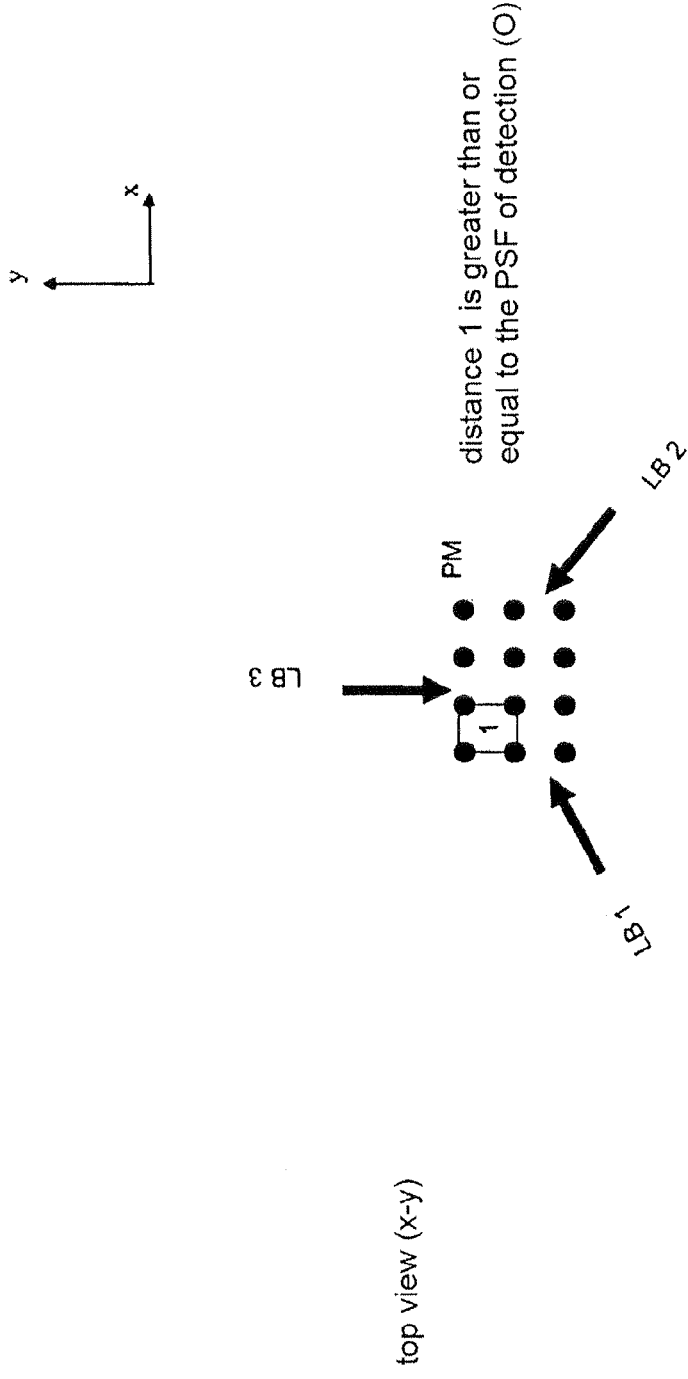
FIG. 5 shows a spot pattern which results when there are three incident light sheets.

When two beams are used, interference results in a striped activation which is localized in x and z. As is shown in FIG. 5, when there are more than two, advantageously three, incident light sheets LB 1 to LB 3 (120° angle), a spot pattern PM results, i.e., an activation localized in x, z and y, so that the distance (1) between the activated fluorescence emitters is greater than or equal to the width of the PSF of detection (O in FIG. 4a). The fluorescence excitation can preferably also be carried out by means of one or more light sheets so that out-of-focus autofluorescence is again prevented.

The fluorescence excitation from direction O in FIG. 4a can also be structured in one or more directions and, for example, can also have a hole pattern (structuring in x and y). In this way, it can be ensured that the distance between the fluorescence emitters is greater than or equal to the width of the detection PSF. A structuring of this kind can be carried out, for example, with a grid structure (DE 10257237A1) or with a multi-spot excitation (DE102006017841).

Further, the photoactivation can be carried out by means of the objective lens O and the fluorescence excitation can be realized with a plurality of light sheet beams which form an interference pattern of the kind described above. Molecules which were activated with overlapping Airy disks are accordingly excited to differing degrees. Also, gaps in the camera image are prevented in this way. Autofluorescence generated by the activation beam can be temporally and/or spectrally separated. After recording a plane, a deactivation must be carried out over the sample area for three-dimensional recordings.

When the photoactivation is carried out through the objective lens O, the structured activation can also be realized by means of special imaging (e.g., of a grid, as was described above) or by a scan mechanism. The light beam can scan over the image field for this purpose, for example, and its intensity changes during the movement, e.g., by a fast AOTF, in such a way that an activation pattern is formed in the focus plane, for example, corresponding to FIG. 5. However, molecules outside of the focus plane are also activated in this method. Nevertheless, by means of a lateral light sheet fluorescence excitation, it can be ensured that only fluorescence from the focus plane is detected. However, after a plane is recorded, a deactivation must be carried out over the sample area for three-dimensional recordings. The intensity of the activation beam is ideally selected in such a way that only one molecule per activation spot (approximately corresponding to the PSF size) is excited on statistical average. This decreases the likelihood that two molecules with overlapping Airy disks will be activated simultaneously. Of course, the activation pattern must be phase-shifted over the course of the image recording so that all of the molecules are activated at the same time. A temporal and/or spectral separation can be carried out by means of the autofluorescence generated by the activation beam. However, the activation intensities are generally so small that autofluorescence should not play a part.

The photoactivation beam and fluorescence excitation beam can be interchanged. This has the advantage that no photoactivation takes place outside the focus plane. Further, the activation can be carried out without structuring by the light sheet and the excitation can be carried out in a structured manner so as to be adapted to the PSF by means of the objective lens. Accordingly, molecules which were activated with overlapping Airy disks are excited to different degrees. Gaps in the camera image can also be prevented in this way. However, the problem of out-of-focus autofluorescence arises here.

A problem in all of the variants described above is posed by the axial resolution which is generally determined in the SPIM method by the width of the light sheet that is used. Since the NA used to generate it is, as a rule, much smaller than the NA of the detection objective lens, this directly results in the problem of a sharply elongated system PSF (lateral extent determined by the resolution of the PALM method (nanometer range), axial extent determined by the light sheet width (micrometer range)). This causes disadvantages for three-dimensional imaging. This problem can be circumvented with the help of the multi-view technique (recording of stacks from different angles) known from the prior art, and an efficient, extensively homogeneous spatial resolution can be generated corresponding to the lateral PALM resolution.

Figure 6:
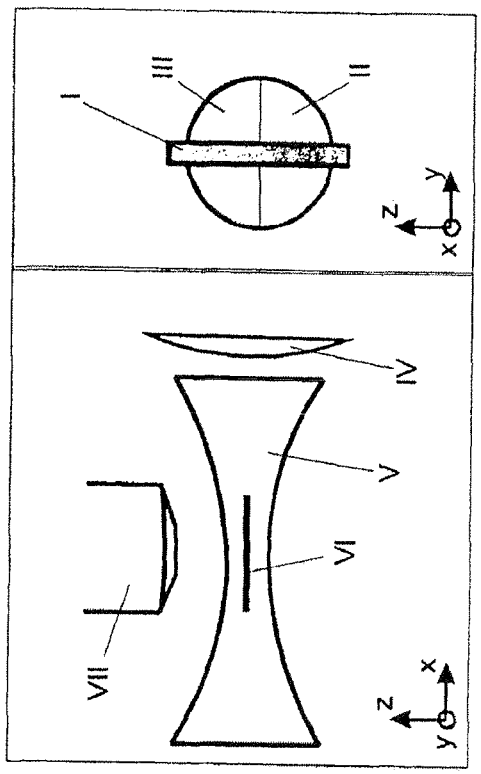
FIG. 6 shows a light sheet which is structured in such a way that it has a zero position in the focus plane over the area of the image region to be observed.

It has proven particularly advantageous when the photoactivated molecules in the edge areas of the light sheet used for activation are deactivated again by another structured light sheet within the meaning of a nonlinear interaction to achieve a higher z-resolution. This can be carried out by means of one of the methods described above, preferably by a switching process. A light sheet can also be used as the deactivating beam, but, as is shown in FIG. 6, the light sheet is structured in such a way that it has a zero position in the focus plane over the area of the image region to be observed. The pupil intensity distribution (I) of the light sheet beam corresponds in this instance to a line which was generated beforehand through suitable optics (e.g., with a Powell lens). A phase-shifting plate (II) having, over one half of the line, a region (III) which generates a pi phase jump is arranged in the pupil. The light sheet (V) extending in the x-y plane is generated by suitable optics (IV). In the range of the field of focus of the illumination optics (IV), a zero position plane (VI) results parallel to the focus plane of the detection optics (VII) in which no molecules are de-excited. Accordingly, corresponding to the STED-type method, the axial extent of the light sheet with photoactivated molecules can be sharply limited in a nonlinear manner and the axial resolution can be improved.

Figure 7:
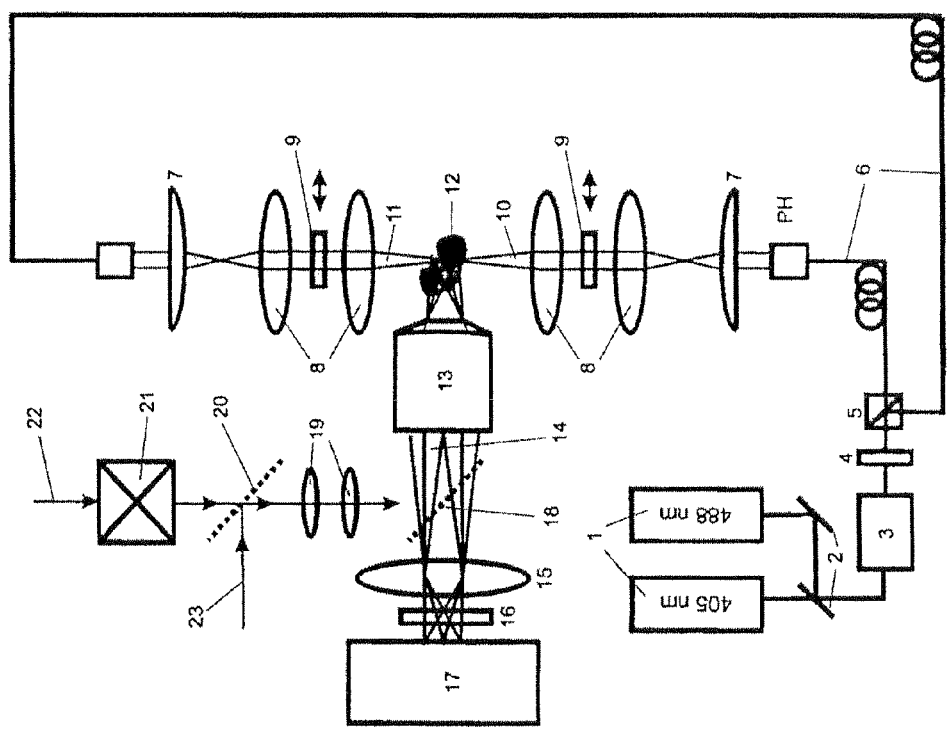
FIG. 7 shows a general optical embodiment example for using methods and applications with photoactivation/photodeactivation by means of a light sheet and CCD widefield detection.

FIG. 7 shows a general optical embodiment example for using the above-described advantageous methods and applications with photoactivation/photodeactivation by means of a light sheet (structured in x-direction) and CCD widefield detection.

The sample is labeled, for example, with Dronpa and can be switched on (activated) over 405 nm and excited and switched off again at 488 nm. The lasers (1) are provided for 405 nm (photoactivation) and 488 nm (fluorescence excitation and photodeactivation) and are combined by a beam combiner (2) and dichroic mirrors. One and the same wavelength can also be used for photoactivation and fluorescence excitation as was mentioned above in the example referring to DENTRA. Accordingly, one laser (405 nm in this case) and the beam combiner (2) can be dispensed with.

An AOTF (3) is used for wavelength selection and for fast switching/attenuation of the laser wavelengths. A rotatable half-wave plate (4) and a polarizing beamsplitter (PBS) (5) with fiber coupling for two channels are preferably arranged downstream of the AOTF (3) in the illumination direction. The output in the two channels can be adjusted by rotating the half-wave plate.

The light is radiated onto the sample (12) via the single-mode fibers (6) by cylindrical optics (7) for generating a light sheet and imaging optics (8) via beam paths (10) and (11), respectively, for the photoactivation (or the deactivation or excitation). The optical path lengths are correspondingly adapted for generating zero positions in the focus plane (x-structuring) according to FIG. 4. A displacement of the standing wave field in the focus plane for illuminating the sample in the intensity minima is carried out by adjusting the relative phase between the two light sheets, for example, by a phase modulator (PH).

The light generated in the sample (12) is detected by a CCD camera via a detection objective lens (13) (microscope objective lens) in a detection beam path (14) via a tube lens (15) and emission filter (16). An optional color splitter (18) which can be swiveled in for inputting a laser (22) or a widefield light source (23) in case the fluorescence excitation is carried out through the detection objective lens is shown in dashed lines in the detection beam path. A mirror (20) which can be swiveled in can optionally be used to choose between laser and widefield light source. The laser (22) and the widefield light source (23) can also be used for activation, in which case a wavelength of 405 nm must be provided instead of a wavelength of 488 nm when DRONPA is used as dye. In particular, a scanner unit (21) which allows a point raster scanning of the image field is provided for the laser beam path (22). Imaging optics (19) which are adapted for this purpose are provided between the scanner unit (21) and the color splitter (18).

Phase-shifting plates (9) can be arranged in the illumination beam paths for the z-structuring of the light sheet described above with reference to FIG. 6.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. An apparatus comprising:
a diffraction-limited resolution volume configured to contain a sample including a plurality of dye molecules which can be switched between different states, wherein at least one state is fluorescing;
an objective lens configured to collect the fluorescence; and
an optical system configured to image the fluorescence collected by the objective lens on a spatially resolving detector; and
one or more light sources for emitting a switching radiation to switch a first subset of the dye molecules in the sample and for emitting an excitation radiation to excite the first subset of the dye molecules;
wherein, in at least a portion of the sample, the dye molecules have a distribution density which is greater than the inverse of the diffraction-limited resolution volume;
wherein at least one of the light sources is arranged in such a way that it radiates through the sample;
wherein the apparatus is configured to carry out at least one of a switching and fluorescence excitation of the dye molecules in the sample at least in one direction approximately perpendicular to the optical axis and in the focus of the objective lens, and
wherein a flat light sheet is generated by a focusing arrangement which penetrates through the sample and is at least approximately perpendicular to the optical axis of the objective lens.

2. The apparatus according to claim 1;
wherein the switching is a photoactivation or a photodeactivation of UF.

3. The apparatus according to claim 1;
wherein a control unit is provided for controlling the switching radiation to ensure that the distribution density of UF in the fluorescing state is less than the inverse of the diffraction-limited resolution volume of the apparatus.

4. The apparatus according to claim 1;
wherein a focusing arrangement is provided for the light source for at least one of the switching and the excitation in order to generate a line-like illumination region which extends in the direction of illumination at least in a direction at least approximately perpendicular to the optical axis of the objective lens.

5. The apparatus according to claim 1;
wherein the focusing arrangement is at least one of an astigmatic and an aspherical optical arrangement.

6. The apparatus according to claim 1;
wherein the light sources used for switching and excitation are combined in a light source whose wavelength is switchable.

7. The apparatus according to claim 1;
wherein the light sources used for switching and excitation have the same wavelength.

8. The apparatus according to claim 1;
wherein different light sources with a wavelength for switching and excitation are provided.
9. The apparatus according to claim 1;
wherein a plurality of light sources for at least one of excitation and switching from different directions are provided.
10. The apparatus according to claim 1;
wherein two light sources are provided opposite one another.
11. The apparatus according to claim 1;
wherein at least three light sources radiating from different directions are provided.
12. The apparatus according to claim 1;
wherein a plurality of light sources are formed by splitting the light of a light source.
13. The apparatus according to claim 1;
wherein a plurality of light sources for generating interference have the same wavelengths.
14. The apparatus according to claim 1;
wherein at least one light source is radiated in laterally and suitable optical means are provided which result in a structuring in the detection direction.
15. A method for high spatial resolution imaging of a structure of a sample, having the following steps:
selecting a substance from a group of substances which can be changed by a switching signal at least once from a first state with first optical properties into a second state with second optical properties;
changing a plurality of changing proportions of the substance by the switching signal into the second state, where the switching is performed in such a way that the distance between switched molecules is greater than or equal to the diffraction-limited optical resolution of the microscope;
exciting portions of the substance which are changed into the second state and localizing the molecules by a spatially resolving detector; and
registering an optical measurement signal in a spatially resolved manner by an objective lens with a detector which starts from the dye molecules in the second state;
wherein at least one of the change into the second state and the excitation is carried out at least approximately perpendicular to at least one of the detection direction and the optical axis of the objective lens,
wherein at least one of the excitation or the activation is carried out by means of a light sheet.
16. The method according to claim 15;
wherein the molecules are deactivated from the second state to the first state.
17. The method according to claim 15;
wherein an illumination region which extends in a line-like manner at least in one direction is carried out in the direction of illumination for the light source for at least one of changing into the second state and excitation in means of a focusing arrangement.
18. The method according to claim 15;
wherein an illumination region is a line-shaped light distribution in the field of view of the objective lens.
19. The method according to claim 15;
wherein an illumination region is a flat light sheet in the field of view of the objective lens.
20. The method according to claim 15;
wherein a change into the second state is carried out by photoactivation.
21. The method according to claim 15;
wherein an excitation is carried out by fluorescence excitation.
22. The method according to claim 15; at least one of the preceding claims,
wherein at least one of a photoactivation and a fluorescence excitation is carried out perpendicular to the fluorescence detection.
23. The method according to claim 15, further comprising:
Step 1, where a photoactivation of individual molecules is carried out in that the fluorescence characteristics of the molecules are changed, wherein the activation is carried out in such a way that the distance between activated molecules is greater than or equal to the optical resolution of the microscope,
Step 2, where an excitation of the activated molecules and localization of the molecules is carried out by a spatially resolving detector,
Step 3, where a deactivation of the activated molecules is carried out, and
Step 4, where Steps 1-3 are repeated, wherein a high-resolution image is formed by superimposing detection images.
24. The method according to claim 15, further comprising:
Step 1, where a photoactivation of individual molecules is carried out by at least one light sheet in that the fluorescence characteristics of the molecules are changed,
Step 2, where a deactivation of molecules is carried out by means of a light sheet which is structured in z-direction so that the layer of the activated molecules in z-direction is less extensive than corresponds to the Abbe resolving power of the detection optics or the numerical aperture of the illumination optics,
Step 3, where an excitation of the activated molecules and localization of the molecules is carried out by a spatially resolving detector,
Step 4, where a deactivation of the activated molecules is carried out, and
Step 5, where Steps 1-4 are repeated, wherein a high-resolution image is formed by superimposing detection images.
25. The method according to claim 15;
wherein at least one of an activation and the excitation of a sample region is carried out from one side.
26. The method according to claim 15;
wherein at least one of an activation and the excitation of a sample region is carried out from opposite sides.
27. The method according to claim 15;
wherein an activation and/or excitation of a sample region is carried out from more than two sides, preferably from three sides.
28. The method according to claim 15;
wherein a plurality of light sources for generating interference have the same wavelengths.
29. The method according to claim 15;
wherein a stripe pattern is generated in the sample by two light sources and interference.
30. The method according to claim 15;
wherein a spot pattern is generated in the sample by means of at least three light sources and interference.
31. The method according to claim 15;
wherein a plurality of light sources are formed by splitting the light of a light source.
32. The method according to claim 15;
wherein an excitation is carried out by means of the objective lens and the activation is carried out by means of the light sheet.

33. The method according to claim 15;
wherein the excitation and activation are carried out by the light sheet.

34. The method according to claim 15;
wherein the excitation light is structured.

35. The method according to claim 34;
wherein a structuring is generated by means of a grating arranged in the excitation beam path.

36. The method according to claim 15;
wherein the excitation light has a spot distribution.

37. The method according to claim 15;
wherein an activation is carried out through the objective lens and the excitation is carried out by means of the light sheet, and the activation light has a spot distribution by means of a modulated scanning movement or a grating imaging.

* * * * *